United States Patent
Aoyama et al.

(10) Patent No.: US 7,628,114 B2
(45) Date of Patent: Dec. 8, 2009

(54) METHOD AND DEVICE FOR PRODUCING SANITARY TAMPONS

(75) Inventors: Hiroshi Aoyama, Akashi (JP); Ryoichi Nishigawa, Akashi (JP); Norihiko Sugimoto, Akashi (JP)

(73) Assignee: Hallys Corporation, Akashi-shi (JP)

( * ) Notice: Subject to any disclaimer, the term of this patent is extended or adjusted under 35 U.S.C. 154(b) by 363 days.

(21) Appl. No.: 11/814,309

(22) PCT Filed: Jan. 18, 2006

(86) PCT No.: PCT/JP2006/300639

§ 371 (c)(1),
(2), (4) Date: Jul. 26, 2007

(87) PCT Pub. No.: WO2006/077883

PCT Pub. Date: Jul. 27, 2006

(65) Prior Publication Data

US 2008/0035040 A1 Feb. 14, 2008

(30) Foreign Application Priority Data

Jan. 19, 2005 (JP) ............................. 2005-011375

(51) Int. Cl.
*D05B 3/12* (2006.01)
*D05B 37/04* (2006.01)
*A61F 13/34* (2006.01)
*D05B 23/00* (2006.01)
(52) U.S. Cl. ............... 112/475.08; 28/120; 604/385.18
(58) Field of Classification Search ............ 112/475.01, 112/475.04, 475.07, 475.08, 10, 470.33, 112/470.36, 122, 139, 152, 307; 28/118, 28/120; 602/56; 604/358, 359, 374, 377, 604/385.01–385.18
See application file for complete search history.

(56) References Cited

U.S. PATENT DOCUMENTS

| 2,476,752 | A | * | 7/1949 | McLaughlin | ................. 112/304 |
| 2,715,374 | A | * | 8/1955 | Carrier | .................. 112/470.22 |
| 3,747,543 | A | * | 7/1973 | Fischbein et al. | ............. 112/11 |
| 3,765,348 | A | * | 10/1973 | Jabor et al. | ............. 112/470.05 |
| 3,856,013 | A | * | 12/1974 | Dulle | .......................... 604/369 |
| 3,965,905 | A | * | 6/1976 | Schoenholz et al. | ........... 604/15 |
| 4,318,407 | A | | 3/1982 | Woon | |
| 4,340,556 | A | | 7/1982 | Ciencewicki | |

(Continued)

FOREIGN PATENT DOCUMENTS

EP 1511453 3/2005

(Continued)

*Primary Examiner*—Ismael Izaguirre
(74) *Attorney, Agent, or Firm*—Westerman, Hattori, Daniels & Adrian, LLP (57) ABSTRACT

A production method for producing sanitary tampons implements a cord placement step of placing at least two continuous string-like cords in parallel on surfaces of at least two cotton pad pieces sequentially placed along a sewing line in a sewing direction of a sewing machine, a first cord sewing step of sewing the cord to one of two cotton pad pieces placed in an adjacent manner, a second cord sewing step of sewing the cord to the other of the two cotton pad pieces, and a cord switching step of switching the cords to be sewn to the cotton pad piece between the first cord sewing step and the second cord sewing step.

6 Claims, 12 Drawing Sheets

U.S. PATENT DOCUMENTS

| | | | |
|---|---|---|---|
| 4,563,398 A | 1/1986 | Sustmann | |
| 4,624,668 A | 11/1986 | Siegers | |
| 4,642,108 A | 2/1987 | Sustmann | |
| 4,755,164 A | 7/1988 | Hinzman | |
| 4,816,100 A | 3/1989 | Friese | |
| 4,836,587 A | 6/1989 | Hinzman | |
| 5,084,038 A | 1/1992 | Sheldon | |
| 5,165,152 A | 11/1992 | Kramer | |
| 5,873,971 A | 2/1999 | Balzar | |
| 6,216,620 B1 * | 4/2001 | Shepard | 112/475.17 |
| 6,343,558 B1 * | 2/2002 | Shepard | 112/475.17 |
| 6,511,451 B1 | 1/2003 | Schoelling | |
| 6,682,513 B2 | 1/2004 | Agyapong | |
| 6,719,743 B1 | 4/2004 | Wada | |
| 6,758,839 B2 | 7/2004 | Lochte | |
| 6,837,882 B2 | 1/2005 | Agyapong | |
| 6,889,409 B2 | 5/2005 | Friese | |
| 7,011,033 B2 * | 3/2006 | Sargent et al. | 112/475.17 |
| 7,059,026 B2 | 6/2006 | Friese | |
| 2002/0193722 A1 * | 12/2002 | Maingault et al. | 602/43 |
| 2003/0225389 A1 | 12/2003 | Cassoni | |
| 2008/0154222 A1 * | 6/2008 | Chaffringeon | 604/361 |

FOREIGN PATENT DOCUMENTS

| | | |
|---|---|---|
| EP | 1064901 | 12/2005 |
| JP | 07-000451 | 1/1995 |
| JP | 07-204224 | 8/1995 |
| JP | 2001-008964 | 1/2001 |
| JP | 2005-211428 | 8/2005 |
| JP | 2005-526584 | 9/2005 |
| JP | 08-117283 | 10/2007 |
| WO | 03/101362 | 12/2003 |

* cited by examiner

METHOD AND DEVICE FOR PRODUCING SANITARY TAMPONS

CROSS-REFERENCE TO RELATED APPLICATIONS

This is a US National Stage pursuant to 35 USC § 371 of International Application PCT/JP2006/300639, filed Jan. 18, 2006, and published Jul. 27, 2007, as WO 2006/077883, which is incorporated herein by reference. The benefit of priority is further claimed to Japanese patent application No. 2005-011375, filed Jan. 19, 2005, and published Aug. 3, 2006, as Japanese Laid-open Application No. 2006-198065, which is also incorporated herein by reference.

TECHNICAL FIELD

The present invention relates to an efficient production method for producing a sanitary tampon, and a production device for implementing the production method.

BACKGROUND

A sanitary tampon is known including a small piece-shaped cotton pad piece to which a string-like cord is sewn (for example, see Japanese Patent Laid-Open No. 2001-8964). In the production of such a sanitary tampon, for example, a continuous string-like cord before being cut is supplied along surfaces of cotton pad pieces sequentially placed at predetermined intervals, and then sewing with a sewing machine is performed along the cord. In such a production method, sanitary tampons as intermediate workpieces in the form of a plurality of cotton pad pieces connected via the continuous string-like cord are first obtained. Then, the cord is cut and each cotton pad piece is rolled and housed in an applicator, thereby obtaining a sanitary tampon as a final product.

However, the conventional production method of a sanitary tampon has the following problem. Specifically, the production efficiency of sanitary tampons depends on the performance of the sewing machine for sewing the cord, and in particular, the sewing speed represented by the sewing length achieved per unit time, which makes it difficult to increase production efficiency beyond the performance of the sewing machine.

The present invention is achieved in view of the problem in the conventional method, inter alia, and relates to an efficient production method for producing a sanitary tampon, and a production device for implementing the production method.

SUMMARY

A first example, in accordance with the present invention, provides a production method for producing a sanitary tampon having a small cotton pad piece to which a string-like cord is sewn, which includes placing at least two continuous string-like cords in parallel on surfaces of at least two cotton pad pieces sequentially placed along a sewing line in a sewing direction of a sewing machine, substantially in parallel with the sewing line; sewing the cord to one of two cotton pad pieces placed adjacently; sewing the cord to the other of the two cotton pad pieces; switching the cords each to be sewn to the cotton pad piece between the first cord sewing step and the second cord sewing step; and cutting a machine sewing thread spanning the cord sewn to one of the two cotton pad pieces and the cord sewn to the other of the two cotton pad pieces.

In the production method of a sanitary tampon of the first example, the step of placing the at least two continuous string-like cords is first implemented by placing at least two continuous string-like cords in parallel on the surfaces of at least two small cotton pad pieces arranged sequentially. Then, the step of switching the cords to be sewn to the cotton pad piece is implemented between the first cord sewing step of sewing the cord to one of the two cotton pad pieces placed adjacently, and the step of sewing the cord to the other of the two cotton pad pieces. Then, the step of cutting the machine sewing thread is implemented by cutting the thread spanning the cord sewn to one of the two cotton pad pieces and the cord sewn to the other of the two cotton pad pieces.

According to the production method according to the first example, as compared with a production method of sewing only one continuous string-like cord to cotton pad pieces placed at predetermined intervals, the production rate of sanitary tampons can be increased several fold based on the number of cords, using a sewing machine having the same performance as in the conventional method—i.e., the production rate can be increased by a factor corresponding to the number of cords placed in parallel, as described above.

Therefore, intermediate workpieces in the form of the cotton pad pieces sequentially sewn to each continuous string-like cord can be obtained in parallel according to the number of cords placed in parallel. Thus, production efficiency can be increased twice or three times according to the number of cords placed in parallel. According to the production method of the sanitary tampon of the first example, the production efficiency of the sanitary tampon can be significantly increased.

The second example provides a production device for producing a sanitary tampon having a small cotton pad piece to which a string-like cord is sewn, including: a sewing machine unit including a sewing machine for sewing the cord to the cotton pad piece with a machine sewing thread; a conveying unit for sequentially conveying the cotton pad pieces, and supplying the cotton pad pieces to the sewing machine; a cord supply unit for supplying in parallel at least two continuous string-like cords along surfaces of the cotton pad pieces conveyed by the conveying unit; a cord switching unit for switching the cords to be sewn between two cotton pad pieces conveyed adjacently; and a thread cutting unit for cutting the thread spanning the different cords, in which the cord switching unit has a cord guide that controls positions of the cords in a parallel direction with respect to the cotton pad pieces, and switches the cords placed on a sewing line in a sewing direction of the sewing machine by forward or backward movement of the cord guide in the parallel direction.

The production device of the second example has the cord guide that controls the positions of the cords in the parallel direction with respect to the cotton pad pieces, and switches the cords placed on the sewing line by the forward or backward movement of the cord guide in the parallel direction. The cord switching unit switches the cords to be sewn between the two cotton pad pieces conveyed adjacently.

Accordingly, two or more intermediate workpieces including the cotton pad pieces continuously sewn to the continuous string-like cords can be produced in parallel. Thus, as compared with a production device that sews only one continuous string-like cord to cotton pad pieces placed at predetermined intervals, the production rate of sanitary tampons can be doubled or tripled, etc., according to the number of cords, using a sewing machine having the same performance as in the conventional method-i.e., the production rate can be increased by a factor corresponding to the number of cords placed in parallel as described above. Thus, the production device of the second example can achieve high performance in efficiently producing a sanitary tampon.

DETAILED DESCRIPTION

A method of implementing the cord switching step in accordance with the first embodiment (Embodiment 1) includes a method of moving the sewing machine forward or backward with respect to the cords placed in parallel in a parallel direction of the cords, a method of integrally moving the cotton pad pieces and the cords forward or backward in the parallel direction with respect to the secured sewing machine, or a method of moving the cords forward or backward in the parallel direction with respect to the sewing machine and the cotton pad pieces while maintaining the parallel positional relationship of the cords.

In the cord switching step, the cords are preferably translated in the parallel direction of the cords to switch the cords placed on the sewing line. In this case, the cords are translated with respect to the cotton pad pieces to switch the cords to be sewn to the cotton pad piece, thereby allowing the cord to be sewn to the cotton pad piece substantially at a fixed position.

In the second embodiment (Embodiment 2), the cord switching unit is preferably configured to synchronize with a sewing operation of the sewing machine unit, so as to move the cord guide forward or backward while the sewing machine needle of the sewing machine is retracted from the cotton pad piece and the cord. In this case, while the cord guide translates the cords, stress applied to the sewing machine needle can be decreased to prevent trouble that occurs in the sewing machine unit.

Also it is preferable that the cord supply unit can supply two cords, and the thread cutting unit includes a rotator configured to rotate the two cotton pad pieces around sewn one of the two cords as a rotational central axis substantially one quarter turn in a rotational direction away from the other unsewn one of the two cords, and a cutter placed to be inserted into a gap between the two cords along the surfaces of rotated two adjacent cotton pad pieces, and can cut the thread.

In this case, there is a low risk that the cutter interferes with the cotton pad pieces. Thus, the thread between the cords can be successively cut with a conveying operation of the cotton pad pieces using the cutter fixedly placed in the gap between the two cords.

EMBODIMENT 1

This embodiment relates to a production method and a production device 1 for efficiently producing a sanitary tampon 5. This will be described with respect to FIGS. 1 to 8.

Figure 1:
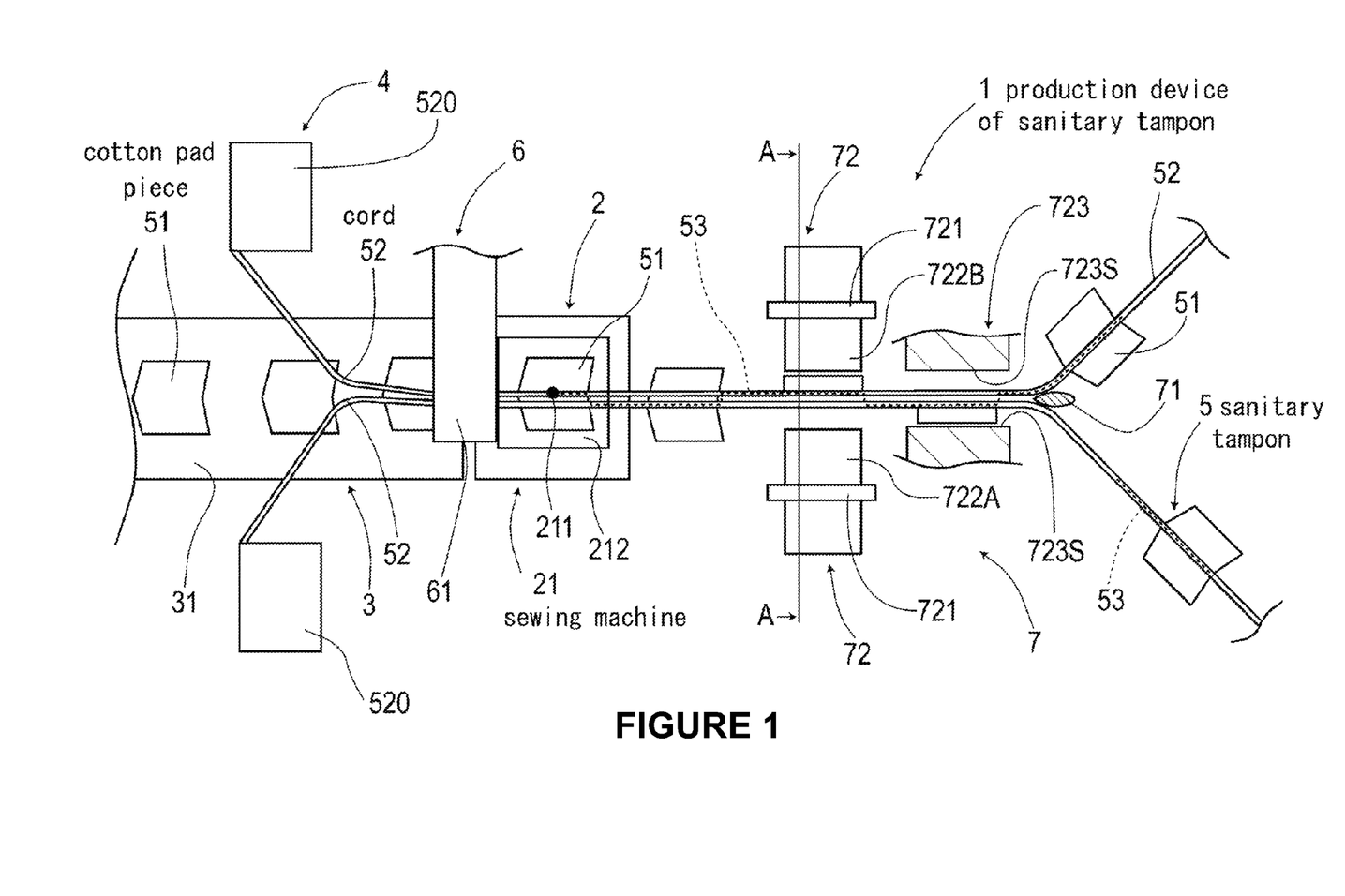
FIG. 1 is a plan view of a production device for producing a sanitary tampon according to Embodiment 1.
Figure 2:
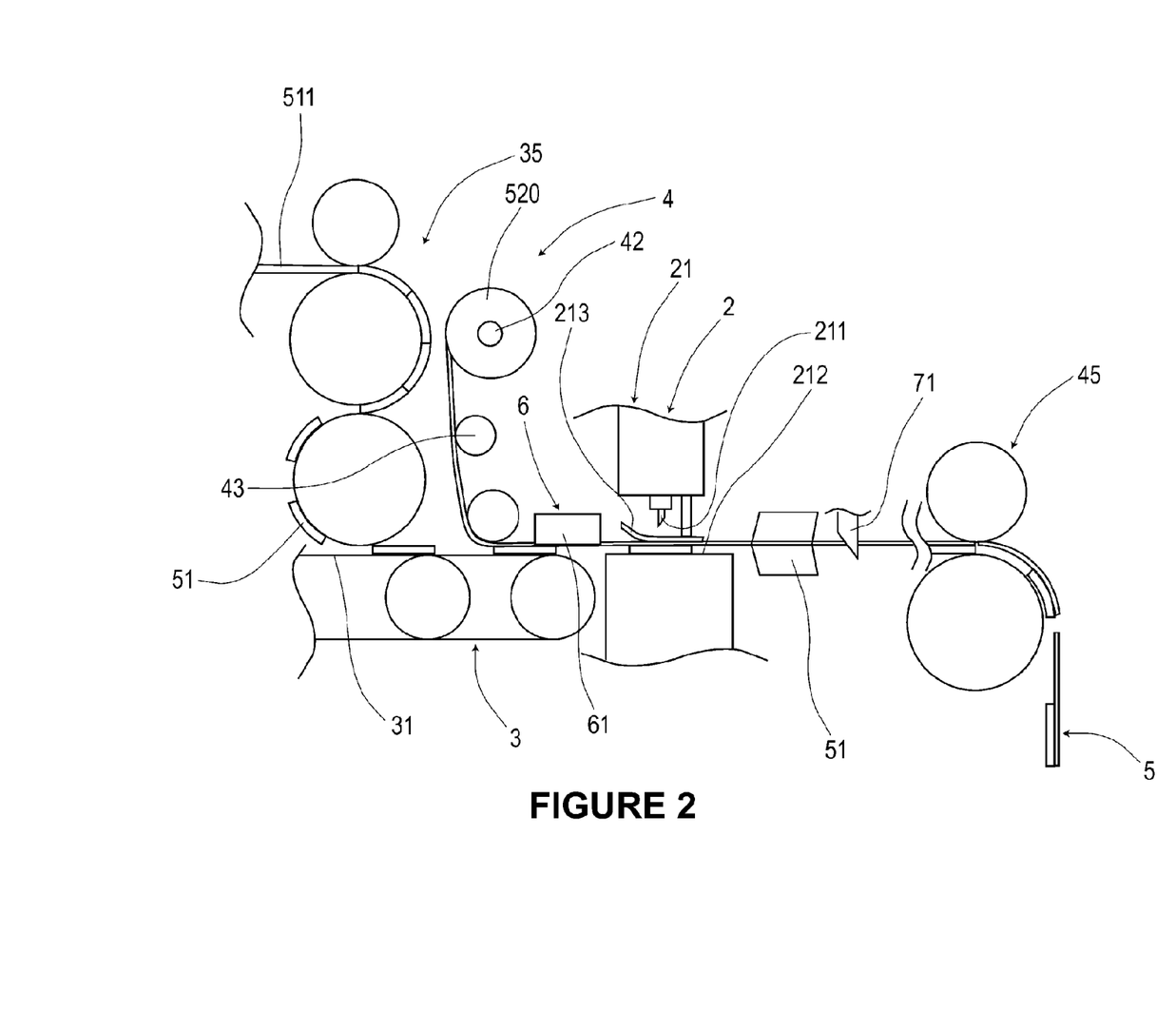
FIG. 2 is a side profile view of the production device for producing a sanitary tampon according to Embodiment 1.

As shown in FIGS. 1 and 2, the production method of the sanitary tampon 5 according to the present embodiment relates to a method for producing the sanitary tampon 5 including a small piece-shaped cotton pad piece 51 to which a string-like cord 52 is sewn. The production method of the sanitary tampon 5 implements a cord placement step of placing at least two continuous string-like cords 52 in parallel on surfaces of at least two cotton pad pieces 51 sequentially placed along a sewing line 20 (see FIG. 5) in a sewing direction of a sewing machine 21, substantially in parallel with the sewing line 20, a first cord sewing step of sewing the cord 52 to one of two cotton pad pieces 51 placed in an adjacent manner, a second cord sewing step of sewing the cord 52 to the other of the two cotton pad pieces 51, a cord switching step of switching the cords 52 to be sewn to the cotton pad piece 51 between the first cord sewing step and the second cord sewing step, and a separation step of cutting a thread 53 spanning the cord 52 sewn to one of the two cotton pad pieces 51 and the cord 52 sewn to the other of the two cotton pad pieces 51.

Figure 3:
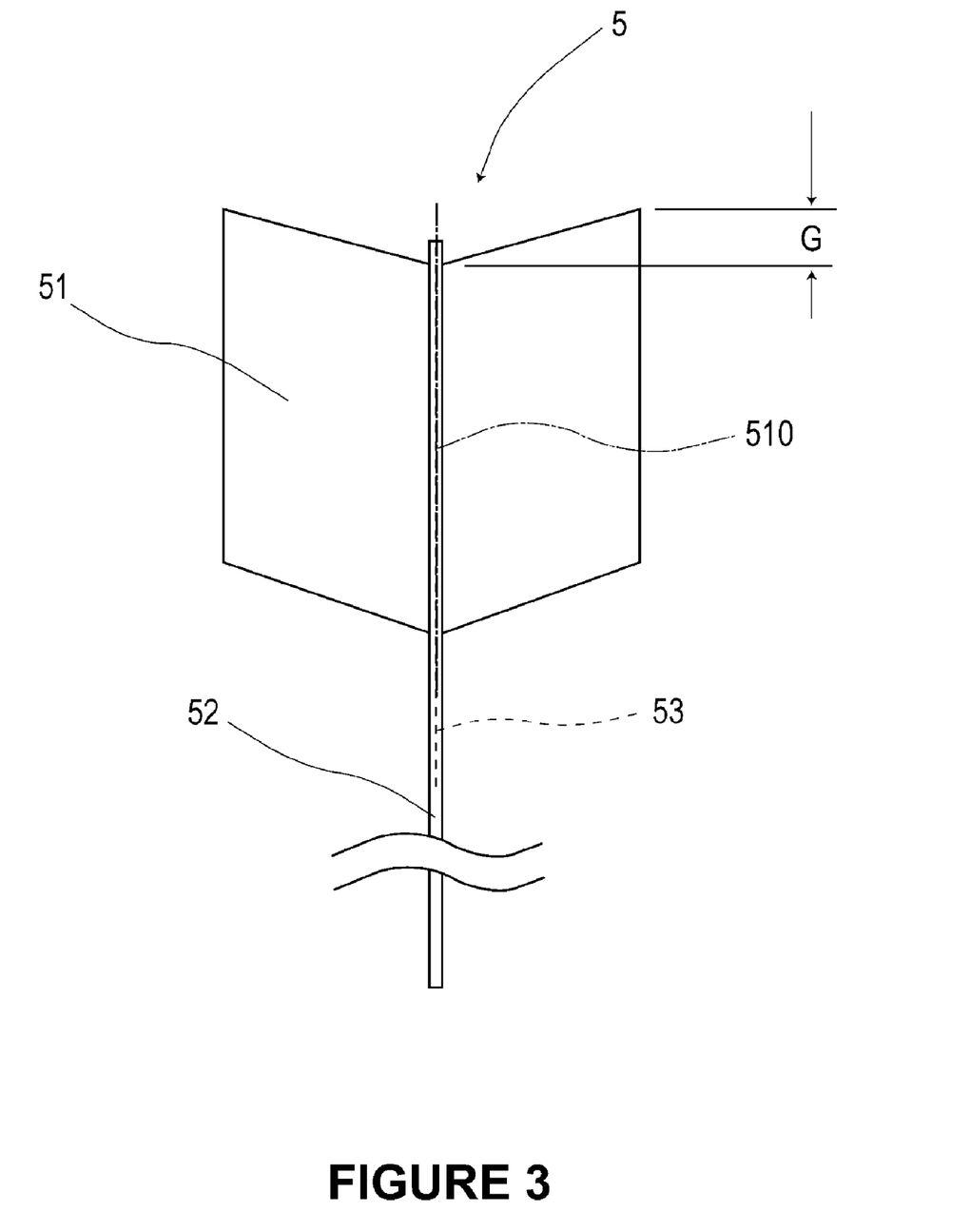
FIG. 3 is a front profile view of the sanitary tampon in Embodiment 1.

Now, this will be described in detail. First, the sanitary tampon 5 in the present embodiment will be described. As shown in FIG. 3, the sanitary tampon 5 includes the small piece-shaped cotton pad piece 51 to which the cord 52 is sewn along the centerline 510 of the cotton pad piece 51. The sanitary tampon 5 as a final product includes the cotton pad piece 51 rolled along the centerline 510, and inserted into and housed in an unshown substantially cylindrical applicator.

The cotton pad piece 51 in the present embodiment is formed by covering laminated cotton pads and rayon pads with nonwoven fabric. The cotton pad piece 51 has a substantially rectangular sheet shape, and is symmetric with respect to the centerline 510. One end crossing the centerline 510 has a recessed wedge shape. The other end crossing the centerline 510 has a protruding wedge shape so as to match the cut shape of the recessed wedge shape of one end.

As shown in FIG. 3, the cord 52 of cotton is sewn to the cotton pad piece 51 along the centerline 510 by the thread 53 that is a machine sewing thread. In the present embodiment, the thread 53 of cotton is used. A tip of the cord 52 on the side of the recessed-wedge-shaped end is positioned within a distance G of a recess of the recessed wedge shape. Specifically, the tip of the cord 52 is positioned between a portion away from the centerline 510 and protruding outward along the centerline 510 and a bottom portion of the recessed wedge shape on the centerline 510. This prevents the cord 52 from protruding beyond the tip of the rolled cotton pad piece 51 in the sanitary tampon 5 as the final product. On the other hand, a tip of the cord 52 on the side of the protruding-wedge-shaped end is positioned so as to extend about 140 mm beyond the protruding-wedge-shaped end of the cotton pad piece 51. In the sanitary tampon 5 produced in the present embodiment, the sewn area by the thread 53 includes a portion overlapping the cotton pad piece 51 and extends to a position at a midpoint of the cord 52 extending on the side of the protruding-wedge-shaped end.

Next, the production device 1 for producing the sanitary tampon 5 will be described. As shown in FIGS. 1 and 2, the production device 1 of a sanitary tampon of the present embodiment includes a sewing machine unit 2 including a sewing machine 21 for sewing the cord 52 to the cotton pad piece 51 with the thread 53 that is the machine sewing thread, a conveying unit 3 for sequentially conveying the cotton pad pieces 51, and sequentially supply the cotton pad pieces 51 to the sewing machine unit 2, the cord supply unit 4 provided to supply two continuous string-like cords 52 in parallel along the surfaces of the cotton pad pieces 51 conveyed by the conveying unit 3, a cord switching unit 6 for switching the cords 52 to be sewn between the two cotton pad pieces 51 conveyed in an adjacent manner, and a thread cutting unit 7 for cutting the thread 53 spanning the different cords 52.

As shown in FIGS. 1 and 2, the cord switching unit 6 has a cord guide 61 that controls positions of the cords 52 in a parallel direction. The cord switching unit 6 can switch the cords placed on the sewing line 20 (see FIG. 5) that is in the sewing direction of the sewing machine 21 by forward or backward movement of the cord guide 61 in the parallel direction. Now, features of the production device 1 will be described in more detail.

Figure 4:
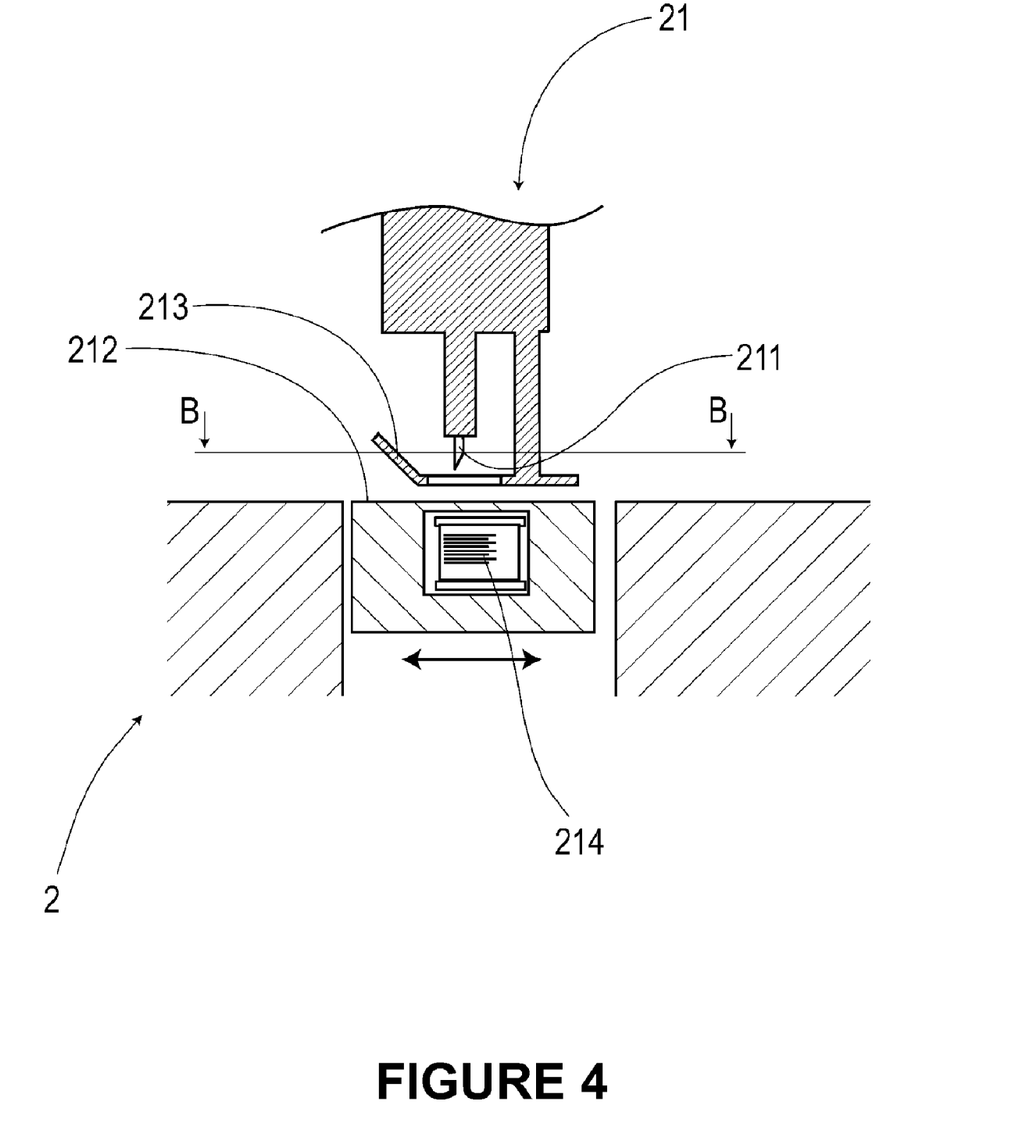
FIG. 4 is a partial cutaway view of a sectional structure of a sewing machine in Embodiment 1.
Figure 5:
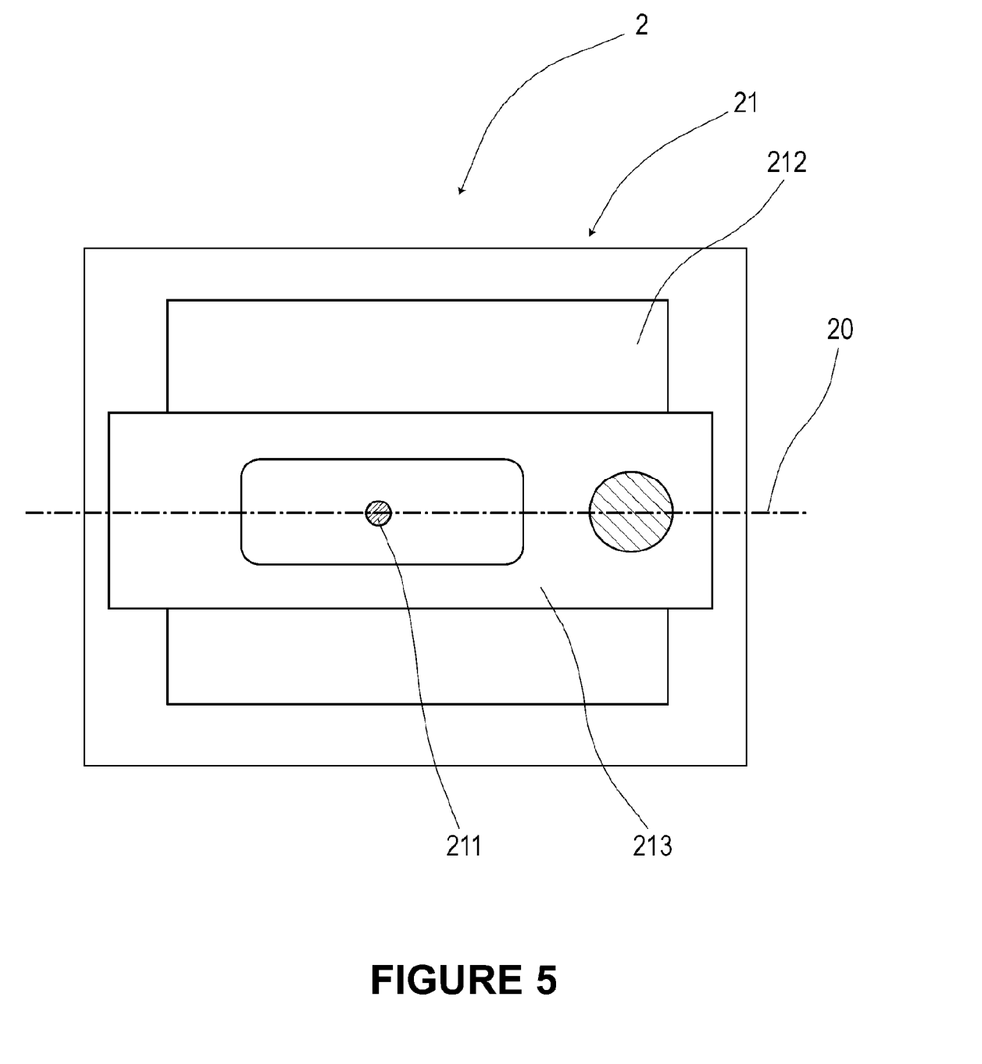
FIG. 5 is a plan view of the sewing machine in Embodiment 1 (a view taken along the arrow direction of the line B-B in FIG. 4)

As shown in FIGS. 4 and 5, the sewing machine 21 in the sewing machine unit 2 includes a sewing machine needle 211 that supports a thread 53 as a needle thread, a rotating hook 214 that houses a thread 53 as a bobbin thread, a sewing machine bed 212 that oscillates in synchronization with a stroke of the sewing machine needle 211, and conveys the cotton pad pieces 51 placed thereon, and a footer 213 that integrally holds the cord 52 and the cotton pad piece 51 with the sewing machine bed 212. The sewing machine 21 in the present embodiment can perform sewing substantially linearly along the sewing line 20 in the sewing direction of the thread 53. The footer 213 has a ski shape, and a tip of the ski shape is directed to an upstream side in the sewing line 20. The footer 213 has a through hole in a substantially flat portion that presses an object to be sewn, and the stroke of the sewing machine needle 211 is performed in the through hole.

As shown in FIGS. 1 and 2, the conveying unit 3 has a conveyor belt 31 that holds and conveys the cotton pad pieces 51. A surface of the conveyor belt 31 has a suction hole connected to an intake port of an unshown vacuum pump. The conveyor belt 31 can suck and hold the cotton pad piece 51 with the suction hole under negative pressure. In the present embodiment, the conveying unit 3 can convey the cotton pad pieces 51 along the centerline 510 with the recessed-wedge-shaped end of the cotton pad piece 51, that is, the end on which the cord 52 does not protrude in the sanitary tampon 5 as a final product (see FIG. 3) on the front side.

As shown in FIG. 2, the production device 1 of the present embodiment includes a cutting unit 35 (omitted in FIG. 1) for sequentially cutting the small piece-shaped cotton pad pieces 51 from a continuous cotton pad sheet 511, provided upstream of the conveying unit 3. The cutting unit 35 has a cut and slip mechanism. The cut and slip mechanism transfers the small piece-shaped cotton pad pieces 51 sequentially cut from the cotton pad sheet 511 to the conveying unit 3 at predetermined intervals.

As shown in FIGS. 1 and 2, the cord supply unit 4 in the present embodiment supplies the two continuous string-like cords 52 in parallel on the surfaces of the cotton pad pieces 51 conveyed to the conveying unit 3 substantially in parallel with the sewing line 20 (see FIG. 5). The cord supply unit 4 includes a reel shaft 42 that holds a bobbin 520 around which the cord 52 is wound, and a tensioner 43 that applies predetermined tension to the cord 52. On the tip of the cord 52 opposite to the reel shaft 42, a cord cutter 45 (omitted in FIG. 1) that cuts the cord 52 for each sanitary tampon 5 is provided. The cord cutter 45 integrally holds the cotton pad piece 51 and the cord 52 extending on the side of the recessed-wedge-shaped end of the cotton pad piece 51, and cuts the cord 52 in a cutting position near the recessed-wedge-shaped end.

The production device 1 may be provided without the cord cutter 45. In this case, intermediate workpieces in the form of the cotton pad pieces 51 sequentially sewn to the continuous string-like cords 52 can be obtained. Individual sanitary tampons 5 can be obtained from the intermediate workpieces by cutting the cord in a downstream process.

Figure 6:
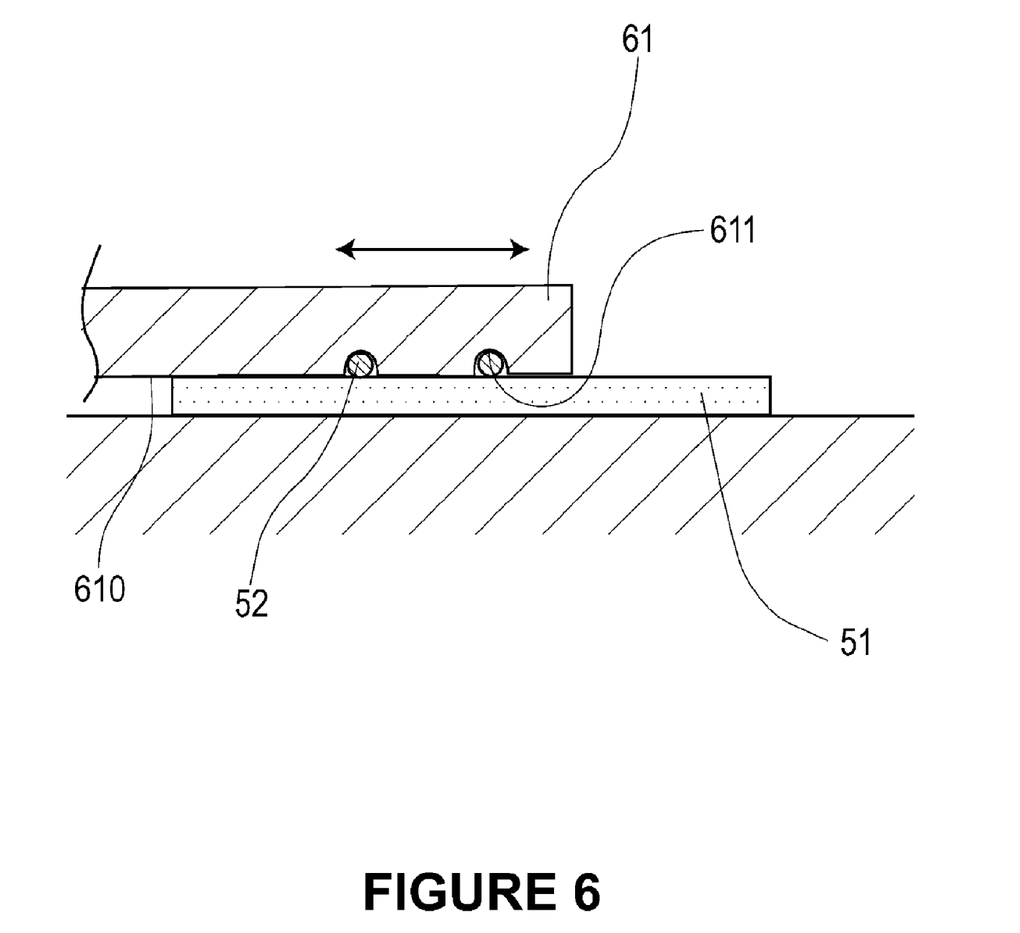
FIG. 6 is a partial cutaway view of a cord guide in Embodiment 1 (a section taken in a parallel direction of cords)
Figure 7:
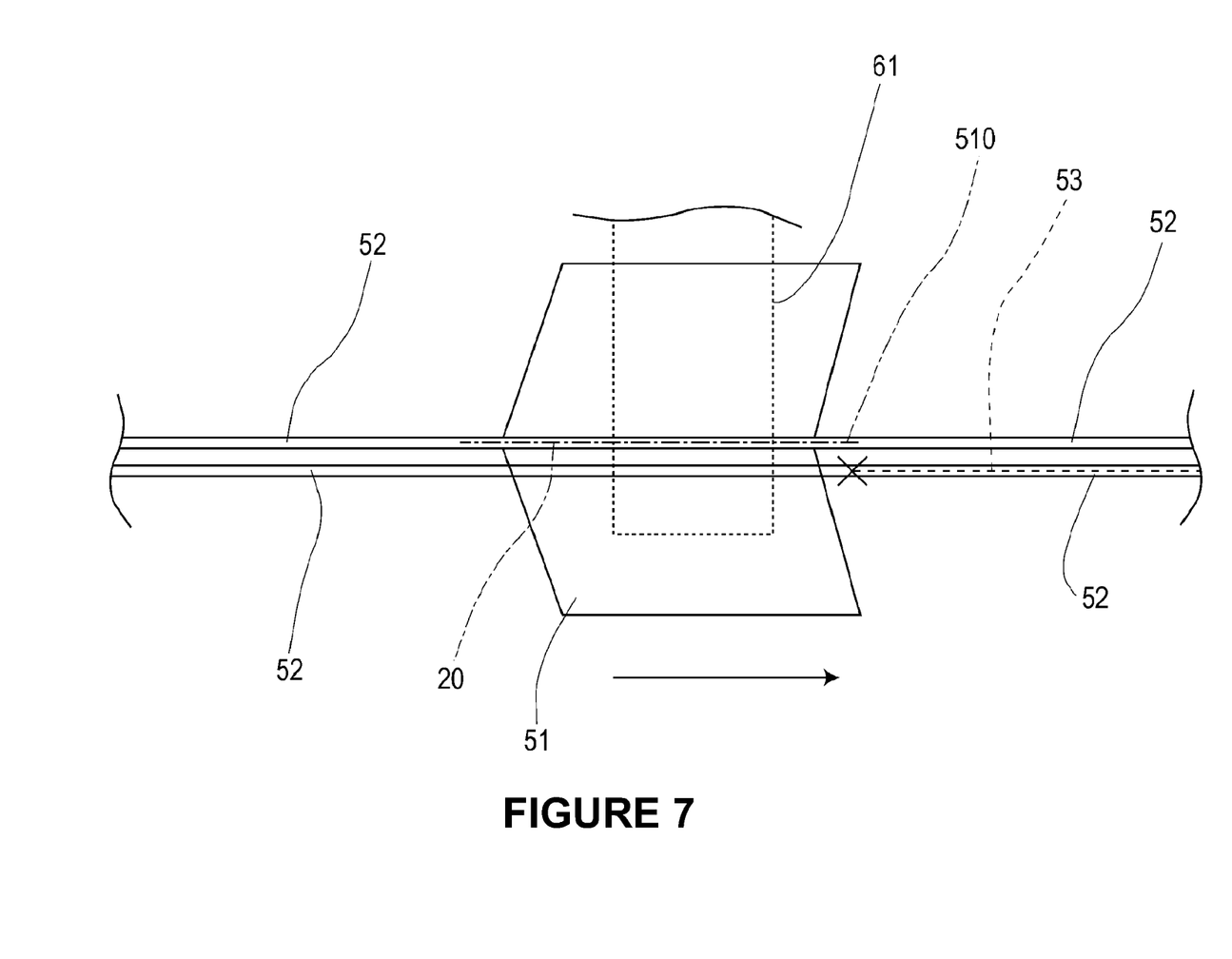
FIG. 7 illustrates an operation of the cord guide in Embodiment 1.

As shown in FIGS. 6 and 7, the cord switching unit 6 can switch the cords 52 to be sewn between the two cotton pad pieces 51 conveyed in an adjacent manner. The cord switching unit 6 in the present embodiment has the cord guide 61 that integrally holds the two cords 52 placed in parallel along the surfaces of the cotton pad pieces 51. The cord guide 61 has two cord grooves 611 that hold the cords 52 in a surface 610 facing the cotton pad pieces 51. The cord guide 61 is moved forward or backward in the parallel direction of the two cords 52 (the arrow direction in FIG. 6), and the forward or backward movement causes the cords 52 placed on the sewing line 20 (see FIG. 5) of the sewing machine 21 to be switched.

As described above, the cord switching unit 6 in the present embodiment is provided, as shown in FIG. 7, to move the cord guide 61 forward or backward to switch the cords 52 to be sewn in a position immediately before the recessed-wedge-shaped end of the cotton pad piece 51 (the position with the mark X in FIG. 7) so as to sew the entire cord 52 with the thread 53 in the sanitary tampon 5 as the final product.

Further, it is also effective to configure the cord switching unit 6 so that the cord guide 61 is moved forward or backward in synchronization with a vertical stroke of the sewing machine needle 211 of the sewing machine unit 2. In this case, there is no risk that the cord guide 61 is moved forward or backward when the sewing machine needle 211 passes through the cord 52. Thus, as compared with the case where the cord switching unit 6 and the sewing machine unit 2 are operated without synchronization, stress can be decreased that may be applied to the sewing machine needle 211 according to the forward or backward movement of the cord guide 61. The cord 52 in the present embodiment is made of soft material, and thus even in the case where the cord switching unit 6 and the sewing machine unit 2 are operated without synchronization, the operation and effect of the present embodiment can be sufficiently obtained though the stress applied to the sewing machine needle 211 may be slightly increased.

Figure 8:
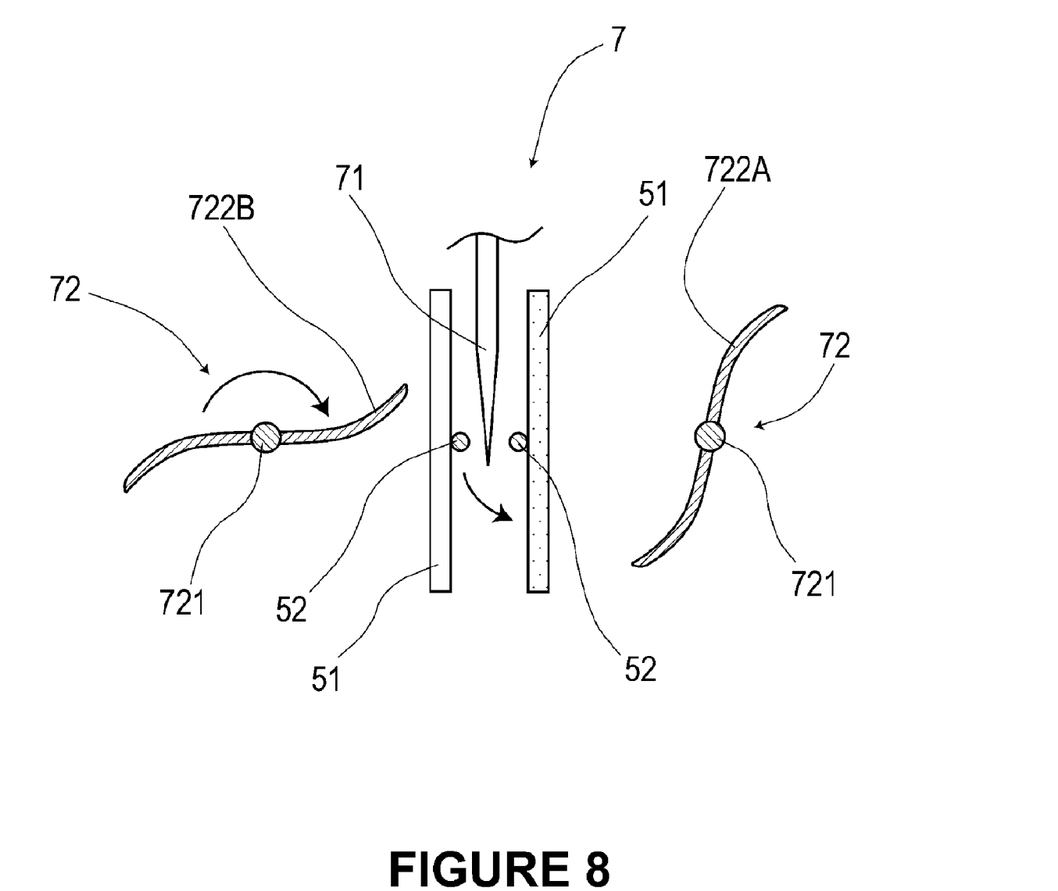
FIG. 8 illustrates an operation of a thread cutting unit in Embodiment 1 (a view taken along the arrow direction of the line A-A in FIG. 1)

As shown in FIGS. 1, 2 and 8, the thread cutting unit 7 includes a cutter 71 for cutting the thread 53. In particular, the thread cutting unit 7 in the present embodiment includes a rotator 72 (omitted in FIG. 2) for rotating the cotton pad piece 51 to which the cord 52 is sewn clockwise or counterclockwise selectively about 90 degrees (about one quarter turn), and a suction mechanism 723 that sucks the rotated cotton pad piece 51 (omitted in FIG. 2).

The suction mechanism 723 has two suction surfaces 723S facing each other with a certain gap therebetween. Each suction surface 723S has a plurality of suction holes communicating with an unshown vacuum pump. The suction mechanism 723 can suck the cotton pad piece 51 with each suction surface 723S so as to hold the rotating position of the cotton pad piece 51 rotated by the rotator 72.

The rotator 72 can rotate each cotton pad piece 51 around one of the cords 52 that is sewn as a rotational central axis substantially one quarter turn in a rotational direction away from the other of the cords 52. As shown in FIGS. 1 and 8, the rotator 72 has a pair of rotors each having a section of a curved plate shape and a rotating shaft 721 provided along the central axis. The rotating shaft 721 is connected to an unshown control motor, and the rotors 722A and 722B are rotatable according to a rotation of the control motor. In each of the rotors 722A and 722B, a portion radially outward around the rotating shaft 721 acts as an arm for rotating the cotton pad piece 51. Specifically, the rotors 722A and 722B each interfere with a portion on the near side of the sewn cord 52 and rotate the cotton pad piece 51.

The rotors include a first rotor 722A that rotates the cotton pad piece 51 clockwise about 90 degrees, and a second rotor 722B that rotates the cotton pad piece 51 counterclockwise 90 degrees. The first rotor 722A is placed on the right in the conveying direction of the cotton pad piece 51, and can be rotated counterclockwise. The first rotor 722A rotates clockwise the cotton pad piece 51 to which the cord 52 on the left in the conveying direction of the cotton pad piece 51 is sewn among the cords 52 placed in parallel.

As shown in FIG. 8, the second rotor 722B is placed on the left in the conveying direction of the cotton pad piece 51, and may be rotated clockwise (in the rotational direction shown by the arrow in FIG. 8). The second rotor 722B rotates counterclockwise (in the rotational direction shown by the arrow in FIG. 8) the cotton pad piece 51 to which the cord 52 on the right in the conveying direction of the cotton pad piece 51 is sewn among the cords 52 placed in parallel.

As shown in FIGS. 1, 2 and 8, the cutter 71 is provided in a position inserted in a gap between the two cords 52 along the surfaces of the two cotton pad pieces 51 placed in an adjacent manner rotated as described above. The cutter 71 can successively cut the thread 53 spanning the different cords 52 with the conveying operation of the cotton pad pieces 51 sequentially sewn to the continuous string-like cords 52. The cotton pad piece 51 is rotated by the rotator 72 as described above and is substantially parallel with the cutter 71. Thus, there is low risk that the cotton pad piece 51 is damaged by interference with the cutter 71.

Next, a procedure for producing the sanitary tampon 5 using the production device 1 will be described. In production of the sanitary tampon 5 using the production device 1 of the present embodiment, the continuous cotton pad sheet 511 before cut is first set in the cutting unit 35, and the bobbin 520 around which the cord 52 is wound is set on the reel shaft 42 of the cord supply unit 4. The tip of cord 52 is set in the cord cutter 45 via the tensioner 43 of the cord supply unit 4, the cord guide 61 of the cord switching unit 6, and the footer 213 of the sewing machine unit 21.

When the operation of the production device 1 is started in this state, the cutting unit 35 first sequentially cuts the small piece-shaped cotton pad pieces 51 from the cotton pad sheet 511. Then, the cut cotton pad pieces 51 are sequentially placed on the surface of the conveyor belt 31 of the conveying unit 3. The cutting unit 35 in the present embodiment includes the cut and slip mechanism. Thus, the cut cotton pad pieces 51 are placed on the surface of the conveyor belt 31 at predetermined intervals.

The cotton pad pieces 51 on the conveyor belt 31 are conveyed toward the sewing machine unit 2. At this time, the cord 52 is unwound from the bobbin 520 in synchronization with the advance of the cotton pad pieces 51. Thus, the cord placement step is implemented, and the cotton pad pieces 51 and the two cords 52 placed in parallel on the surfaces of the cotton pad pieces 51 are continuously fed into the gap between the footer 213 and the sewing machine bed 212 in the sewing machine unit 2. At this time, in the present embodiment, the cotton pad pieces 51 are supplied to the sewing machine unit 2 so that the centerline 510 of the cotton pad piece 51 is substantially aligned with the sewing line 20 (see FIG. 5) in the sewing direction of the sewing machine 21.

One of the two cords 52 whose positions in the parallel direction are controlled by the cord guide 61 is substantially aligned with the centerline 510 of the cotton pad piece 51 and the sewing line 20. Thus, the first cord sewing step of sewing one of the two cords 52 to the cotton pad piece 51 is implemented. The sewing machine bed 212 oscillates and further advances the cotton pad piece 51 along the sewing line 20. Thus, one of the two cords 52 is sewn along the centerline 510 of the cotton pad piece 51.

Then, as shown in FIG. 7, when the sewing position (marked with an 'X' in FIG. 7) by the sewing machine 21 reaches a position near the recessed-wedge-shaped end at the tip of the cotton pad piece 51, the cord guide 61 is moved forward or backward in the parallel direction of the cord 52. Thus, the cord switching step is implemented, and then the other of the two cords 52 different from the cord in the first cord sewing step is placed on the sewing line 20 of the sewing machine 21. In the present embodiment, the cord guide 61 is moved forward or backward when the sewing machine needle 211 is retracted away from the cotton pad piece 51, and pulled out of the cotton pad piece 51 and the cord 52. Thus, in the production device 1 of the present embodiment, there is low risk that stress is applied to the sewing machine needle 211 in switching the cords 52.

As described above, the other cord 52 placed on the sewing line 20 of the sewing machine 21 is sewn to a new cotton pad piece 51, and the second cord sewing step is implemented. Then, the sewing of the cotton pad piece 51 is finished, and the cord guide 61 is moved forward or backward in the parallel direction of the cord 52 in a position immediately before the recessed-wedge-shaped end at a tip of the next cotton pad piece 51. Thus, the cord switching step is again implemented.

The cotton pad piece 51 ejected from the sewing machine unit 2 is supplied to the thread cutting unit 7. In the thread cutting unit 7, the rotator 72 first rotates each cotton pad piece 51 about 90 degrees around the sewn cord 52 as a rotational central axis. In the present embodiment, the cotton pad piece 51 to which the cord 52 on the right in the conveying direction of the cotton pad piece 51 is sewn is rotated counterclockwise 90 degrees. Also, the cotton pad piece 51 to which the cord 52 on the left in the conveying direction of the cotton pad piece 51 is rotated clockwise 90 degrees.

Thus, each cotton pad piece 51 is rotated 90 degrees to prevent interference between the cutter 71 for cutting the thread 53 placed to be inserted into the gap between the cords 52 placed in parallel and the cotton pad piece 51. When the cotton pad piece 51 is conveyed and advanced in this state, the thread 53 spanning the two cords 52 reaches the position of the cutter 71. Then, when the cotton pad piece 51 is further advanced, the thread 53 is caught and cut by the cutter 71, and the separation step is implemented.

Thus, two rows of intermediate workpieces in the form of the cotton pad pieces 51 sequentially sewn to the continuous string-like cords 52 can be obtained. In the present embodiment, the cords 52 are cut by the cord cutter 45 placed downstream of the thread cutting unit 7 to obtain individual sanitary tampons 5. It may be allowed that the cord cutter 45 is omitted from the production device 1 of the present embodiment and a device for producing the intermediate workpiece is configured. In this case, the cords 52 can be separately cut to obtain individual sanitary tampons 5.

EMBODIMENT 2

This embodiment is based on the production device of a sanitary tampon of Embodiment 1 with a different configuration of the thread cutting unit. This will be described with reference to FIG. 9.

Figure 9:
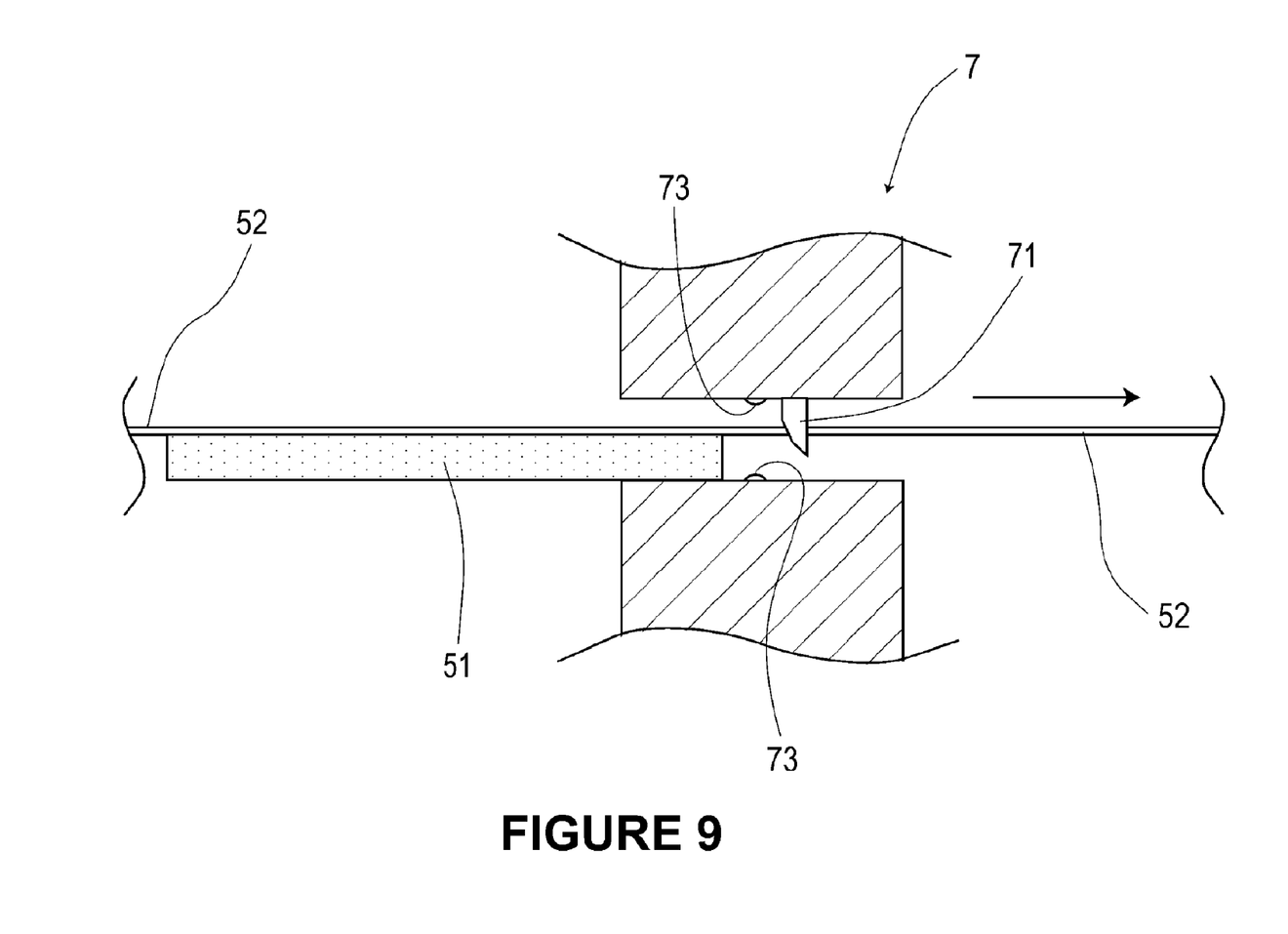
FIG. 9 is a side profile view of a thread cutting unit in accordance with Embodiment 2.

The thread cutting unit 7 in the present embodiment has no rotator for rotating a cotton pad piece 51 unlike the thread cutting unit 7 in Embodiment 1. The thread cutting unit 7 in the present embodiment has a mechanism that cuts a thread 53 spanning cords 52 while preventing interference with the cotton pad piece 51 in place of the rotator.

The thread cutting unit 7 in the present embodiment has a cutter 71 that is moved forward or backward toward a gap between the cords 52 placed in parallel. The forward or backward movement of the cutter 71 is controlled by an unshown control unit. The thread cutting unit 7 has an optical sensor 73 for detecting the presence of an object in a direction passing through the gap between the cords 52 placed in parallel. The optical sensor 73 inputs an output signal to the control unit.

The control unit detects approach of the cotton pad piece 51 based on the output signal of the optical sensor 73, and retract the cutter 71 in a position immediately before a recessed-wedge-shaped end. The control unit then detects passage of the cotton pad piece 51 to advance and protrude the cutter 71. Thus, the thread 53 spanning the two cords 52 is cut while preventing interference with the cotton pad piece 51.

Figure 10:
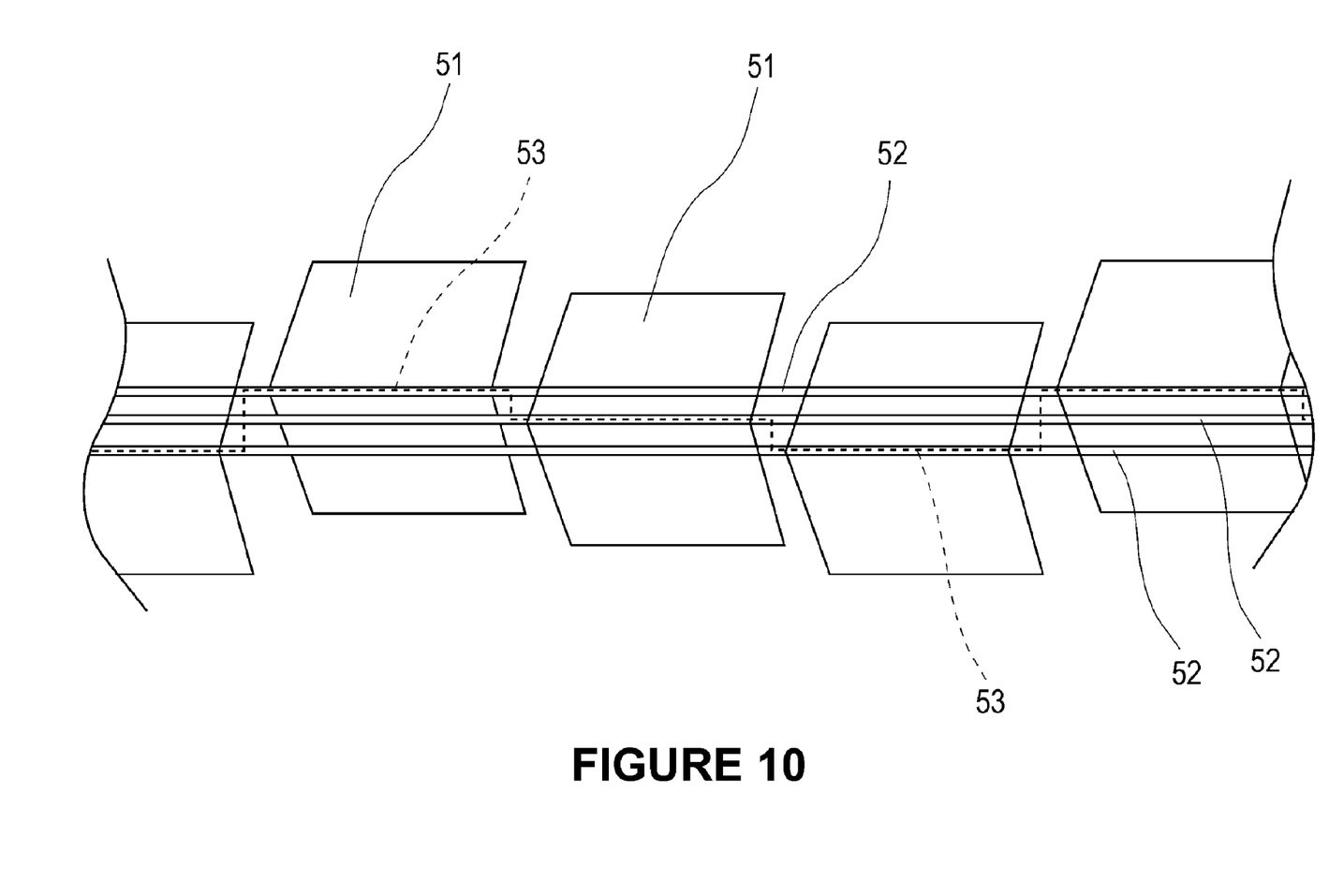
FIG. 10 is a plan view of another production device of a sanitary tampon in accordance with Embodiment 2.

As the optical sensor 73, an image sensor can be used. Further, in place of the optical sensor 73, a contact sensor that physically detects contact with the cotton pad piece 51 can be used. Also, if thread cutting units 7 in the present embodiment are placed in parallel, the thread cutting units 7 can be applied to a production device in which, as shown in FIG. 10, three of more cords are supplied in parallel on surfaces of cotton pad pieces 51 sequentially conveyed, and three or more rows of intermediate workpieces (in the form of the cotton pad pieces sequentially sewn to the continuous string-like cords) are produced in parallel. Other features and the operation and effect may be the same as in Embodiment 1.

EMBODIMENT 3

The third embodiment (Embodiment 3) is based on the production device of Embodiment 1 with a different configuration of the cord switching unit. This will be described with reference to FIG. 11. The cord switching unit 6 in the third embodiment includes a footer 62 of a sewing machine. Specifically, in the production device in the third embodiment, the footer 62 is moved forward or backward in a direction parallel to the cords 52 to switch the cords 52, each to be sewn to a cotton pad piece.

Figure 11:
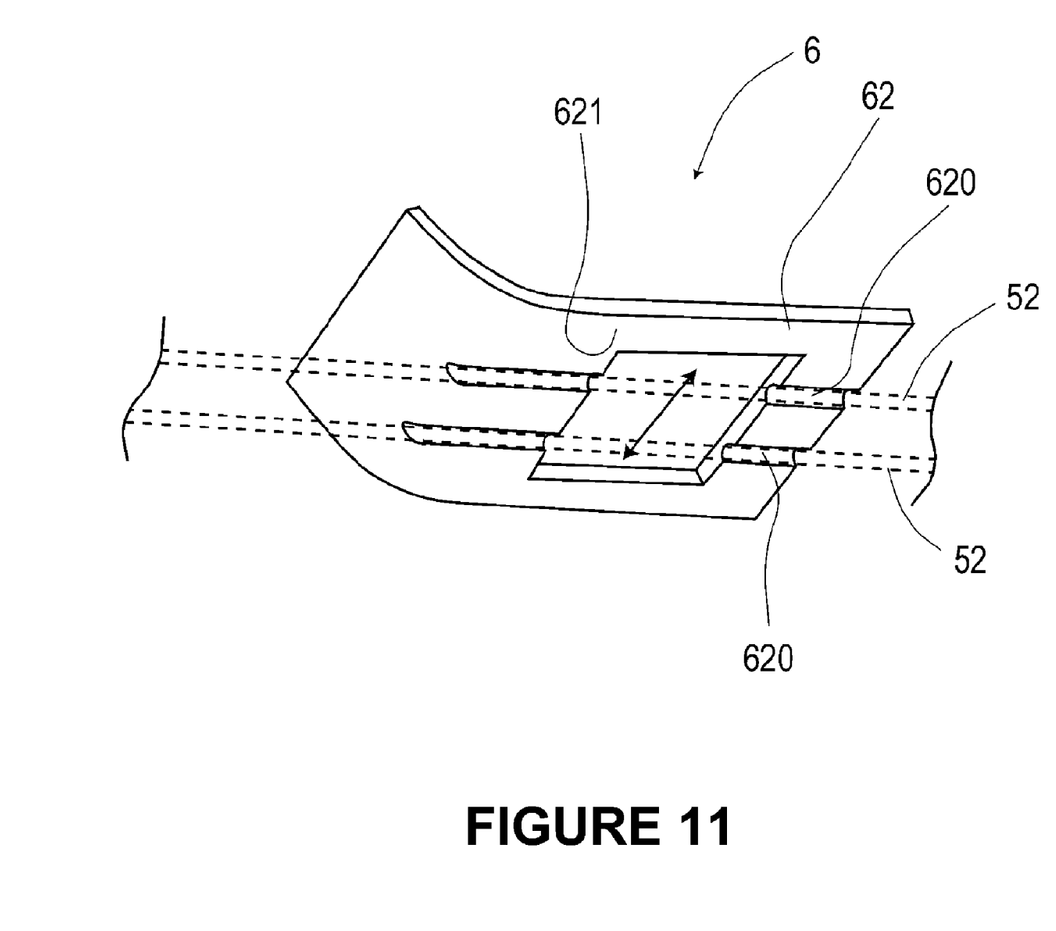
FIG. 11 is a perspective view of a footer provided as a cord switching unit in accordance with Embodiment 3.

As shown in FIG. 11, the footer 62 in the third embodiment has two cord grooves 620 for holding the cord 52 in a holding surface 621 that abuts the cotton pad piece. Also, an unshown forward or backward movement mechanism is connected to the footer 62. The forward or backward movement mechanism is operated to move the footer 62 forward or backward in the parallel direction of the cords 52. It is preferable to move the footer 62 forward or backward in synchronization with a sewing operation of a sewing machine needle and when the sewing machine needle is retracted from the cotton pad piece and the cord 52. In this case, stress applied to the sewing machine needle can be reduced to increase the life of the needle.

Figure 12:
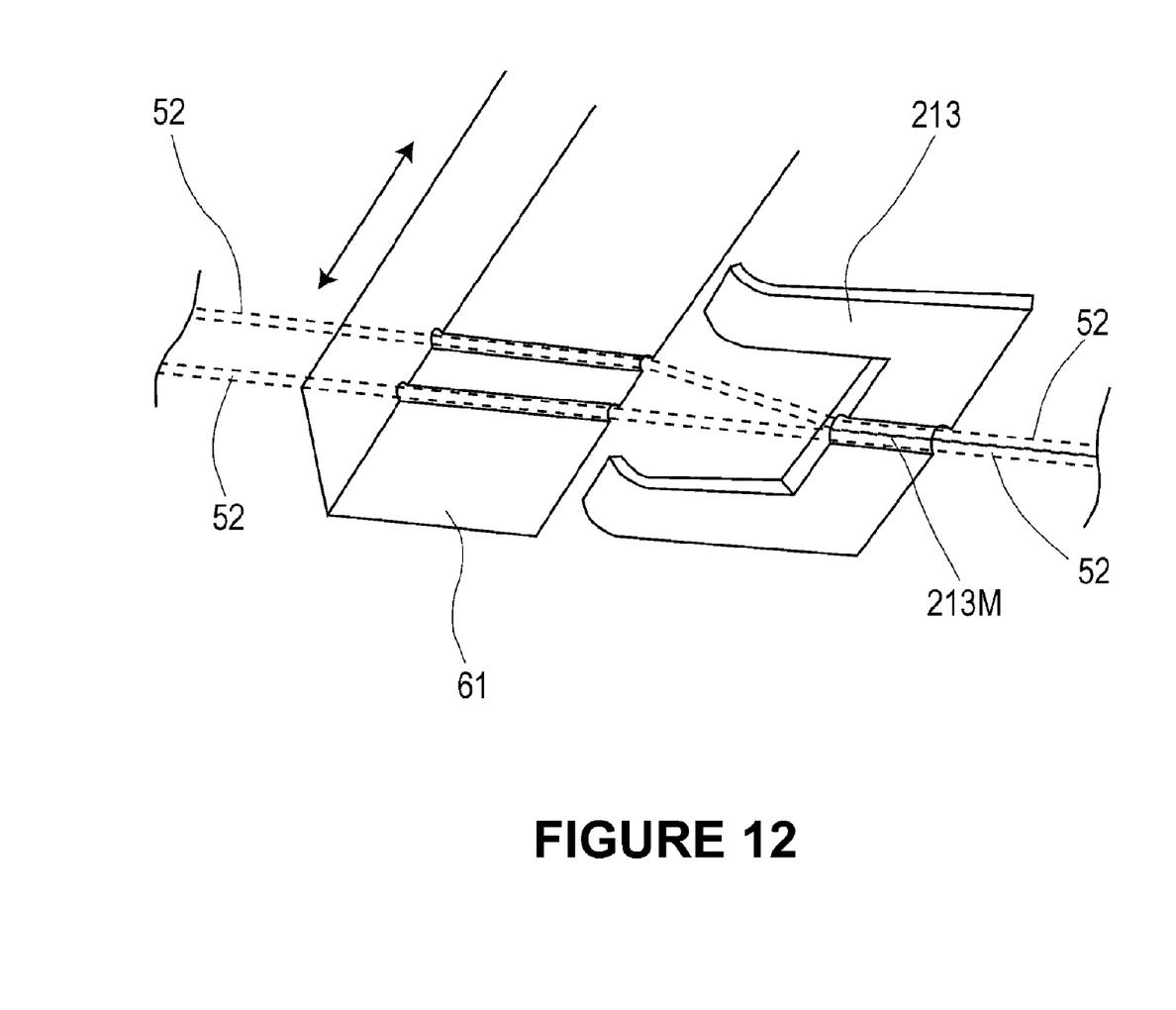
FIG. 12 is a perspective view of another combination of a cord guide and a footer in accordance with Embodiment 3.

Other features and the operation and effect may be the same as in Embodiment 1. Also, as shown in FIG. 12, a footer 213 formed into a substantially C shape to form an opening, and a cord guide 61 placed adjacent to the opening of the footer 213 may be combined. A holding surface of the footer 213 may have a cord groove 213M for holding two cords 52 supplied from the cord guide 61. With such a configuration, the cord guide 61 is moved forward or backward in the arrow direction shown in FIG. 12 to switch the cords 52 to be sewn to the cotton pad piece.

The invention claimed is:

1. A method for producing a sanitary tampon including a small piece-shaped cotton pad piece to which a string-like cord is sewn, comprising:
    a cord placement step of placing at least two continuous string-like cords in parallel on surfaces of at least two cotton pad pieces sequentially placed along a sewing line in a sewing direction of a sewing machine, substantially in parallel with the sewing line;
    a first cord sewing step of sewing the cord to one of two cotton pad pieces placed adjacently;
    a second cord sewing step of sewing the cord to the other of the two cotton pad pieces;
    a cord switching step of switching the cords to be sewn to the cotton pad piece between the first cord sewing step and the second cord sewing step; and
    a separation step of cutting a thread that is a machine sewing thread spanning the cord sewn to one of the two cotton pad pieces and the cord sewn to the other of the two cotton pad pieces.

2. The method for producing a sanitary tampon according to claim 1, wherein in the cord switching step, the cords are translated in a parallel direction of the cords to switch the cords placed on the sewing line.

3. A production device for producing a sanitary tampon including a small piece-shaped cotton pad piece to which a string-like cord is sewn, comprising:
    a sewing machine unit including a sewing machine configured to sew the cord to the cotton pad piece with a thread that is a machine sewing thread;
    a conveying unit configured to sequentially convey the cotton pad pieces, and supply the cotton pad pieces to the sewing machine unit;
    a cord supply unit configured to supply in parallel at least two continuous string-like cords along surfaces of the cotton pad pieces conveyed by the conveying unit;
    a cord switching unit configured to switch the cords to be sewn between two cotton pad pieces conveyed in an adjacent manner; and
    a thread cutting unit configured to cut the thread spanning the different cords,
    wherein the cord switching unit has a cord guide that controls positions of the cords in a parallel direction with respect to the cotton pad pieces, and is configured to switch the cords placed on a sewing line in a sewing direction of the sewing machine by forward or backward movement of the cord guide in the parallel direction.

4. The production device for producing a sanitary tampon according to claim 3, wherein the cord switching unit is configured to synchronize with a sewing operation of the sewing machine unit, so as to move the cord guide forward or backward while the sewing machine needle of the sewing machine is retracted from the cotton pad piece and the cord.

5. The production device for producing a sanitary tampon according to claim 3, wherein the cord supply unit is configured to supply two cords, and wherein the thread cutting unit includes a rotator configured to rotate the two cotton pad pieces around a sewn one of the two cords as a rotational central axis substantially one quarter turn in a rotational direction away from the other unsewn one of the two cords that is not sewn, and a cutter placed to be inserted into a gap between the two cords along the surfaces of two rotated adjacent cotton pad pieces, and configured to cut the thread.

6. The production device for producing a sanitary tampon according to claim 4, wherein the cord supply unit is configured to supply two cords, and wherein the thread cutting unit includes a rotator configured to rotate the two cotton pad pieces around sewn one of the two cords as a rotational central axis substantially one quarter turn in a rotational direction away from the other unsewn one of the two cords that is not sewn, and a cutter placed to be inserted into a gap between the two cords along the surfaces of rotated two adjacent cotton pad pieces, and configured to cut the thread.

* * * * *